(12) United States Patent
Usa et al.

(10) Patent No.: US 11,786,628 B2
(45) Date of Patent: Oct. 17, 2023

(54) AIR PURIFIER

(71) Applicant: Sunstar Engineering Inc., Osaka (JP)

(72) Inventors: Tomoharu Usa, Osaka (JP); Katsuhiro Yamaguchi, Osaka (JP)

(73) Assignee: Sunstar Engineering Inc., Osaka (JP)

( * ) Notice: Subject to any disclaimer, the term of this patent is extended or adjusted under 35 U.S.C. 154(b) by 26 days.

(21) Appl. No.: 17/481,976

(22) Filed: Sep. 22, 2021

(65) Prior Publication Data
US 2022/0088262 A1 Mar. 24, 2022

(30) Foreign Application Priority Data

Sep. 23, 2020 (JP) .................................. 2020-158702

(51) Int. Cl.
*A61L 9/20* (2006.01)
*B01J 35/00* (2006.01)
*B01J 21/06* (2006.01)

(52) U.S. Cl.
CPC ............. *A61L 9/205* (2013.01); *B01J 21/063* (2013.01); *B01J 35/004* (2013.01); *A61L 2209/11* (2013.01); *A61L 2209/12* (2013.01)

(58) Field of Classification Search
CPC ................... B60H 3/0608; B60H 1/12; B60H 2003/0675; B60H 3/0616; B60H 3/0625; B60H 3/0633; B60H 3/0641; B60H 2003/0666; B60H 21/063; B60H 35/004; A61L 9/205; A61L 2209/12; A61L 2209/16; A61L 9/122; A61L 9/20; A61L 9/04; A61L 9/18; A61L 2209/11
See application file for complete search history.

(56) References Cited

U.S. PATENT DOCUMENTS 4,629,482 A * 12/1986 Davis ................ B01D 46/0031
55/385.2
6,589,486 B1 * 7/2003 Spanton .................. F24F 11/30
422/120

(Continued)

FOREIGN PATENT DOCUMENTS

| JP | 11-159034 A | 6/1999 |
|---|---|---|
| JP | 2000-84061 A | 3/2000 |
| JP | 5474612 | 2/2014 |

(Continued)

*Primary Examiner* — Joshua L Allen
*Assistant Examiner* — Shizhi Qian
(74) *Attorney, Agent, or Firm* — Renner, Otto, Boisselle & Sklar, LLP

(57) ABSTRACT

An air purifier according to an aspect of the present disclosure includes: an air passage defined between a first inner wall surface and a second inner wall surface that are planar and face each other, having a flat passage cross section in which a distance between the first inner wall surface and the second inner wall surface is small, and meandering in a plane parallel to the first inner wall surface and the second inner wall surface; a catalyst member including a support having a flat mesh shape, and a photocatalyst supported on the support, the catalyst member being disposed parallel to the first inner wall surface and the second inner wall surface in the air passage; and a plurality of light sources dispersed on the second inner wall surface, and configured to irradiate the catalyst member with light that activates the photocatalyst.

7 Claims, 4 Drawing Sheets

(56) References Cited

U.S. PATENT DOCUMENTS

2015/0064069 A1* 3/2015 Yi .......................... A61L 9/20
                                                                                 422/121
2019/0062180 A1* 2/2019 Taghipour ............... C02F 1/325

FOREIGN PATENT DOCUMENTS

| JP | 2019-17855 | A | | 2/2019 | | |
|----|------------|---|---|--------|---|---|
| JP | 2020-62334 | A | | 4/2020 | | |
| WO | WO-2011135601 | A1 | * | 11/2011 | ............. | A61L 9/205 |

* cited by examiner

US 11,786,628 B2

AIR PURIFIER

RELATED APPLICATION DATA

This application claims the benefit of Japanese Patent Application No. 2020-158702, filed Sep. 23, 2020, the disclosure of which is incorporated herein by reference in its entirety.

BACKGROUND OF THE INVENTION

Field of the Invention

The present disclosure relates to an air purifier.

Related Art

Air purifiers that exert a deodorization effect and a sterilization effect by degrading organic matter by means of a photocatalyst, such as a titanium oxide, have been put in practical use. An air purifier of this type includes a catalyst member that supports a photocatalyst, a light source that irradiates the catalyst member with light that activates the photocatalyst, and an air flow generator that suctions ambient air and brings it into contact with the photocatalyst (see, for example, Patent Document 1).

Such an air purifier including a photocatalyst is required to sufficiently activate the photocatalyst by effectively irradiating the photocatalyst with light, and to efficiently bring air into contact with the photocatalyst. For example, Patent Document 1 discloses an air purifier including a duct in which a fan generates an air flow, a rod-shaped light source provided in the duct and extending perpendicularly to the direction of the air flow, and a photocatalytic sheet provided in the duct and having a cylindrical shape coaxially surrounding the light source.

Patent Document 1: Japanese Patent No. 5474612

SUMMARY OF THE INVENTION

As the air purifiers become more and more popular in general households, there is an increasing demand for reduction in size of the air purifiers. A configuration in which a rod-shaped light source and a cylindrical photocatalytic sheet are disposed perpendicularly to an air flow, as disclosed in Patent Document 1, leads to a large cross-sectional area of an air passage, thereby making it difficult to reduce the size of the entire device. In view of the foregoing, the present disclosure is intended to provide an air purifier that is small and capable of degrading organic matter highly efficiently.

An air purifier according to an aspect of the present disclosure includes: an air passage defined between a first inner wall surface and a second inner wall surface that are planar and face each other, having a flat passage cross section in which a distance between the first inner wall surface and the second inner wall surface is small, and meandering in a plane parallel to the first inner wall surface and the second inner wall surface; a catalyst member including a support having a flat mesh shape, and a photocatalyst supported on the support, the catalyst member being disposed parallel to the first inner wall surface and the second inner wall surface in the air passage; and a plurality of light sources dispersed on the second inner wall surface, and configured to irradiate the catalyst member with light that activates the photocatalyst.

The above-described air purifier may further include a first current plate extending from a side adjacent to the first inner wall surface and a second current plate extending from a side adjacent to the second inner wall surface, the first and second current plates forming a labyrinth structure in an inlet portion of the air passage.

In the above-described air purifier, the plurality of light sources may be received in recesses formed in the second inner wall surface, on a one-to-one basis.

The above-described air purifier may further include an exhaust fan configured to suction air out of the air passage, and a circuit board having the plurality of light sources mounted thereto, and forming end walls of the recesses, A space outside the circuit board may communicate with a passage adjacent to a suction side of the exhaust fan through an opening having a smaller cross-sectional area than the air passage.

The above-described air purifier may further include: a casing having a holding structure that holds the catalyst member; and a smooth guide plate disposed in the casing and forming the first inner wall surface.

The above-described air purifier may further include: an intermediate base forming the second inner wall surface and having an electric element disposed thereon. The casing may have a lower casing that has the guide plate fastened thereto, and an upper casing that is detachably combined with the lower casing, has the intermediate base fastened thereto, and covers the electric element.

In the above-described air purifier, a distance between the catalyst member and the first inner wall surface may be 1 mm or more and 8 mm or less, and a distance between the catalyst member and the second inner wall surface may be 4 mm or more and 12 mm or less, and may be greater than the distance between the catalyst member and the first inner wall surface.

The present disclosure provides an air purifier that is small and capable of degrading organic matter highly efficiently.

DETAILED DESCRIPTION OF THE INVENTION

Figure 1:
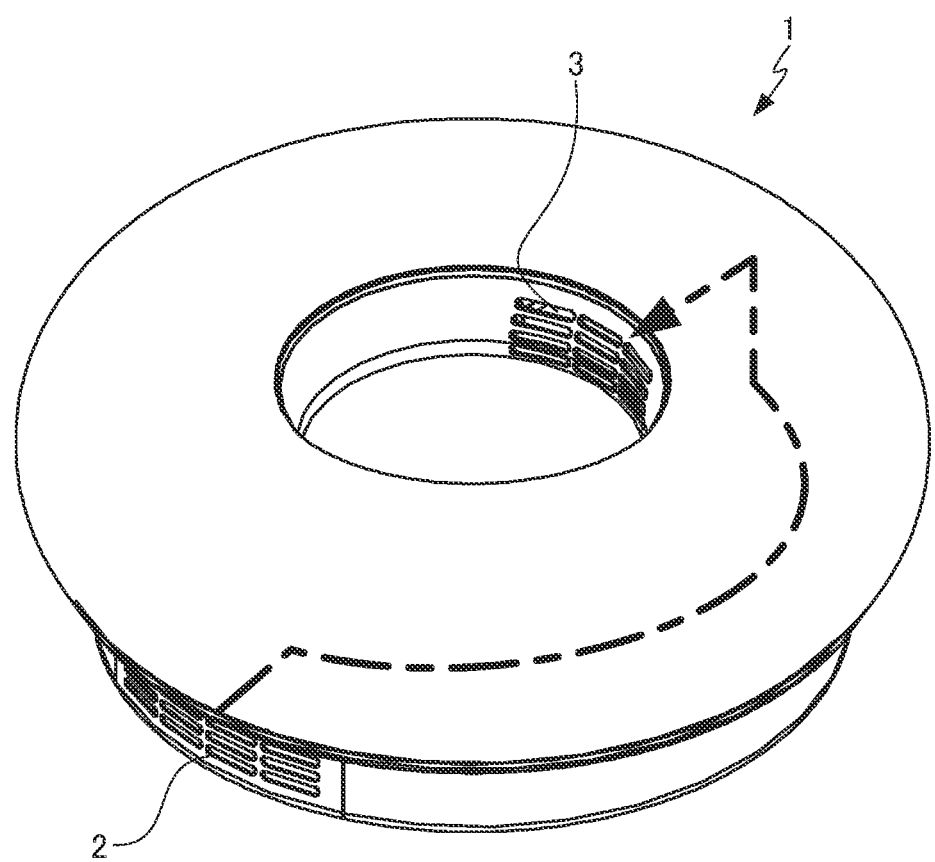
FIG. 1 is a perspective view illustrating an air purifier according to an embodiment of the present disclosure.
Figure 2:
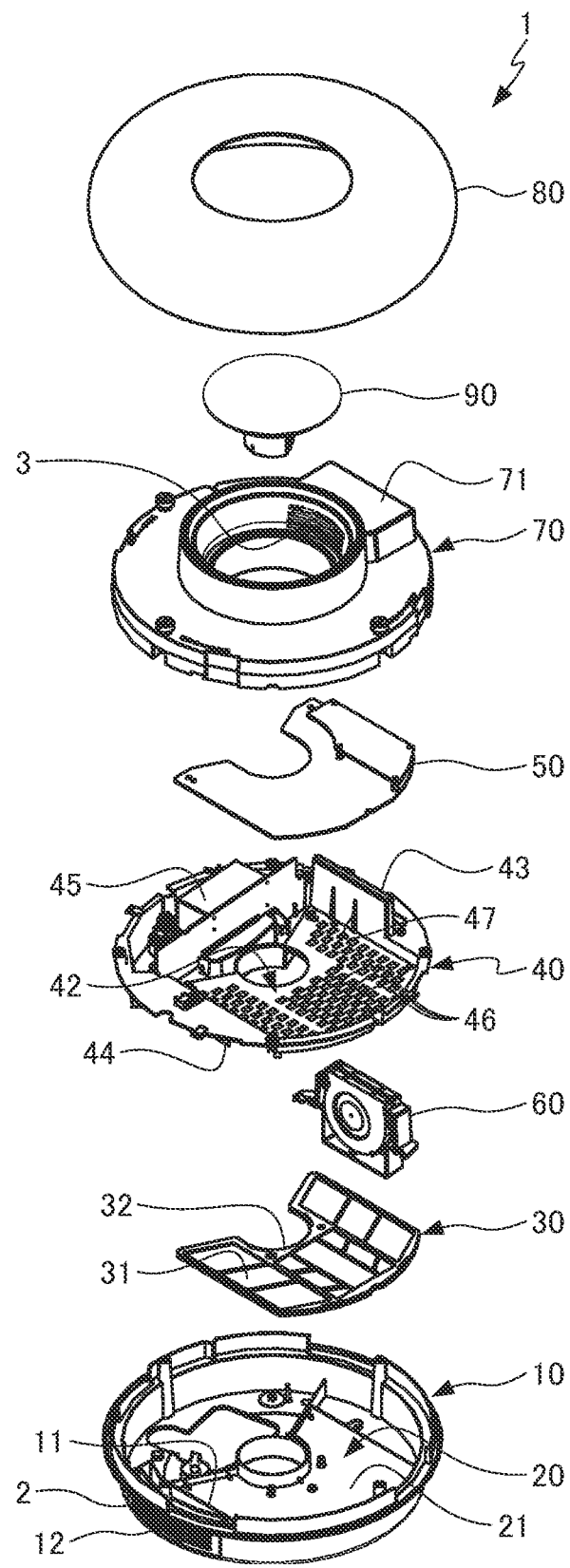
FIG. 2 is an exploded perspective view of the air purifier of FIG. 1.
Figure 3:
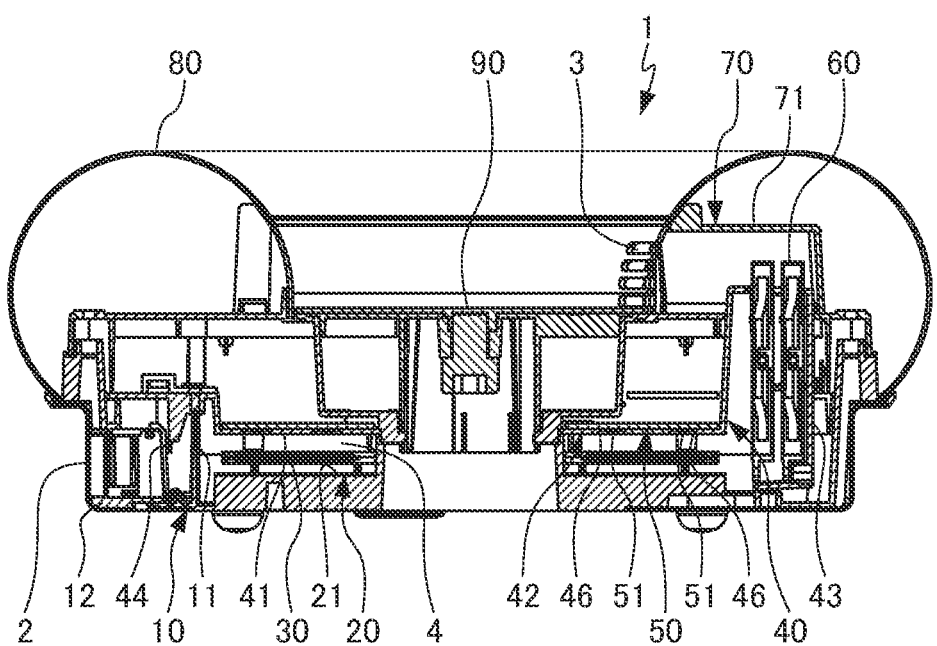
FIG. 3 is a cross-sectional view of the air purifier of FIG. 1.
Figure 4:
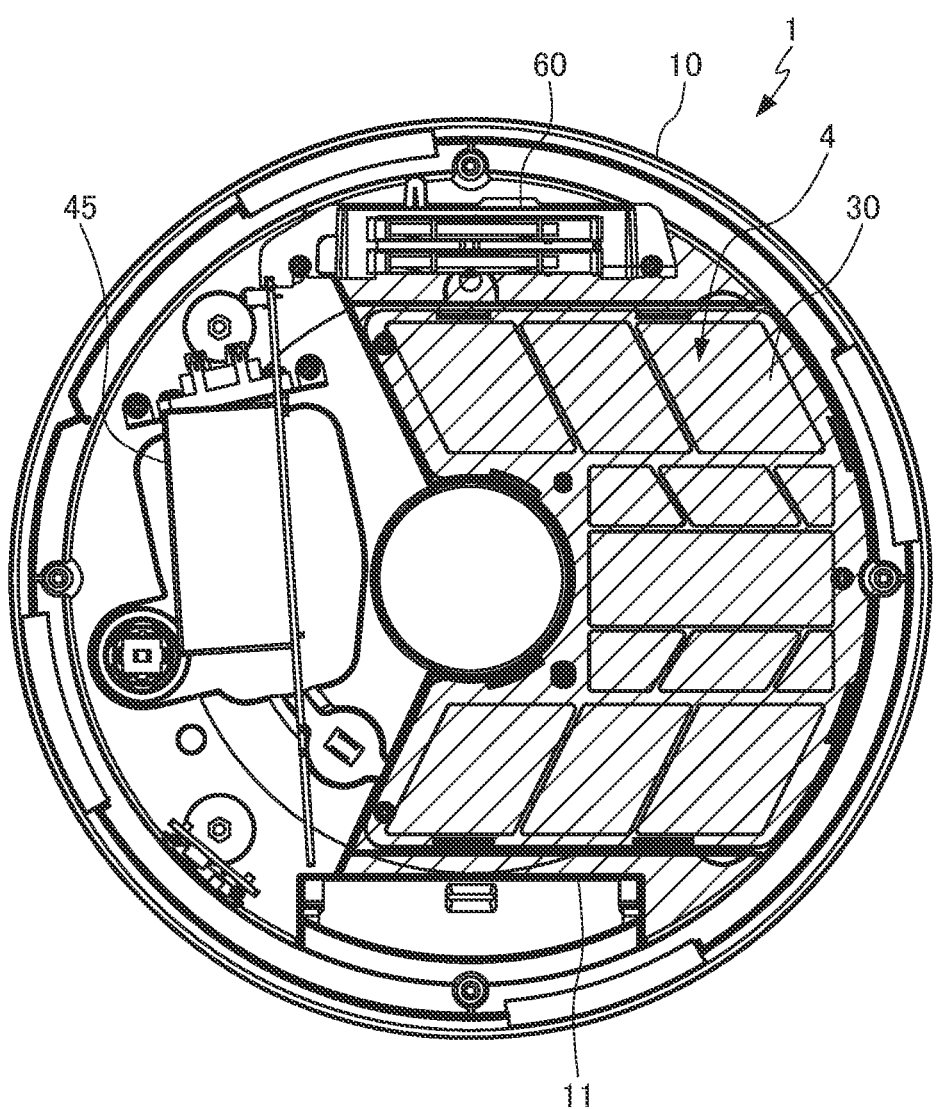
FIG. 4 is a planar view of the air purifier of FIG. 1, having elements of its upper portion detached therefrom.

An embodiment of the present disclosure will be described with reference to the drawings. FIG. 1 is a perspective view illustrating an air purifier 1 according to the present embodiment. FIG. 2 is an exploded perspective view of the air purifier 1. FIG. 3 is a cross-sectional view of the air purifier 1. FIG. 4 is a planar view of the air purifier 1 having elements of its upper portion detached therefrom.

The air purifier 1 illustrated in FIG. 1 is substantially doughnut-shaped. The air purifier 1 has, at a location in its outer peripheral portion, an air inlet 2 through which outside air is suctioned in a radial direction. The air purifier 1 further has, at a location in its inner peripheral portion and opposite to the air inlet 2, an air outlet 3 through which purified air is blown out in a radially inward direction. The air purifier 1 includes an air passage 4 that guides air suctioned through the air inlet 2 in a counterclockwise direction, as indicated by the alternate long and short dash line in FIG. 1. In the following description, for the sake of convenience, positional relationships will be described using words such as "upper/top/upward", "lower/bottom/downward", etc., with reference to the air purifier 1 in one typical use state. Note that the positional relationships and directions described below are not intended to limit an orientation of the air purifier 1 in use.

As illustrated in FIG. 2, the air purifier 1 includes a lower casing 10, a guide plate 20, a catalyst member 30, an intermediate base 40, a circuit board 50, an exhaust fan 60, an upper casing 70, a cover 80, and a decorative central member 90. The lower casing 10 and the guide plate 20 are integrally fastened to each other to constitute a lower half of the air purifier 1. The intermediate base 40, the circuit board 50, the exhaust fan 60, and the upper casing 70 are integrally fastened to each other to constitute an upper half that is attachable to and detachable from the lower half. The catalyst member 30 is held between the lower half and the upper half. Due to this configuration, the lower half and the upper half of the air purifier 1 can be separated from each other when maintenance of the catalyst member 30 is carried out. The cover 80 and the decorative central member 90 are provided for decoration.

As illustrated in FIG. 3, the air passage 4 is defined between a first inner wall surface (bottom surface) 21 that is planer and formed by the guide plate 20, and a second inner wall surface (top surface) 41 that is planar and formed by the intermediate base 40. The lower casing 10 and the intermediate base 40 each have a portion forming a side wall of the air passage 4.

The air passage 4 corresponds to a distance between the first inner wall surface 21 and the second inner wall surface 41, and thus, has a thin and flat passage cross section. Air passing through the flat air passage 4 can efficiently contact with the catalyst member 30 to be described later.

As indicated by hatching in FIG. 4, the air passage 4 meanders in a plane parallel to the first inner wall surface 21 and the second inner wall surface 41. The meander of the air passage 4 can increase a contact area between air and the catalyst member 30, and can reduce variation in a flow rate of air in the air passage 4, thereby facilitating contact of air with the catalyst member 30. The air passage 4 preferably has a meander amount corresponding to 50% or more of an average width of the air passage 4. This configuration makes it impossible to see through to an outlet of the air passage 4 from the inlet of the air passage 4, so that air can be prevented from concentrating in a portion of the air passage 4 and from linearly flowing through. In addition to meandering in its entirety, the air passage 4 may be configured to cause air to flow further uniformly by means of, for example, a partition wall provided in the air passage 4.

The lower casing 10 has therein the guide plate 20 fastened to an inner portion of the lower casing 10 with, for example, a screw. The lower casing 10 has a holding structure that holds the catalyst member 30. The holding structure can include, for example, projections penetrating through the guide plate 20 and extending in the air passage 4, and stepped portions formed on the side wall of the air passage 4. With this holding structure, the lower casing 10 holds the catalyst member 30 such that the catalyst member 30 is spaced apart from the guide plate 20 by a certain distance.

The lower casing 10 has, in an inlet portion of the air passage 4, a first current plate 11 that extends from below (from a side adjacent to the first inner wall surface 21) and stretches over the entire width of the air passage 4. The lower casing 10 has a filter member 12 attached to a portion functioning as the air inlet 2. The filter member prevents ingress of foreign objects. The lower casing 10, which has the complex shape as described above, can be made of a resin molding.

The guide plate 20 can be made of a metal plate, such as an aluminum plate or a stainless-steel plate. The guide plate 20 provides the first inner wall surface 21 that is smooth to allow air to smoothly flow in a space below the catalyst member 30. As will be described later, the guide plate 20 also functions as a reflector plate that reflects light emitted from a side adjacent to the second inner wall surface 41 and passing through openings of the catalyst member 30, so that a back surface of the catalyst member 30 is activated.

The guide plate 20 defines the first inner wall surface 21. This configuration makes it easy to design the lower casing 10. In contrast, an attempt to define the smooth first inner wall surface 21 without employing the guide plate 20 will inconveniently require provision of, for example, ribs or the like on the back surface of the lower casing 10, i.e., an outer surface of the bottom of the air purifier 1, in order to ensure a strength of the lower casing 10.

The catalyst member 30 is disposed parallel to the first inner wall surface 21 and the second inner wall surface 41 in the air passage 4, while being spaced apart from the first inner wall surface 21 by a distance and being spaced apart from the second inner wall surface 41 by a distance. The catalyst member 30 can have a support having a flat mesh shape, a catalyst body 31 including a photocatalyst supported on a surface of the support, and a frame 32 reinforcing the catalyst body 31.

The catalyst body 31 has, as the whole, a mesh shape having a large number of openings allowing light to pass therethrough. The "mesh shape" refers to a sheet shape having a large number of planarly formed openings, and is not limited to a shape formed by combining lengthwise linear members with crosswise linear members. A ratio of the openings (ratio of an area allowing passage of light) of the catalyst body 31 can be set to, for example, 15% or more and 55% or less, and preferably, 20% or more and 50% or less. With this configuration, light emitted from the side adjacent to the second inner wall surface 41 and passing through the catalyst member 30 is reflected by the guide plate 20 toward a lower surface of the catalyst member 30, so that the photocatalysis of the catalyst body 31 is further activated and an effect of degrading organic matter and the like is further enhanced.

Specific examples of the support include a sheet of metal foil having micro apertures randomly formed by etching, a wire mesh, a molded resin mesh, a perforated metal, etc. Nevertheless, an expanded metal is particularly preferably used since it is highly capable of supporting a photocatalyst, and is excellent in mechanical properties and cost efficiency. Producing the support from titanium and subjecting a surface of the support to an oxidation treatment can enhance adhesion between the support and the photocatalyst. Producing the support from aluminum can make the catalyst body 31 relatively inexpensive and excellent in workability.

The photocatalyst is not particularly limited. Anatase-type titanium oxide, which is a material known to have excellent photocatalysis, can be used as the photocatalyst. To attain a large contact area with air, the photocatalyst is preferably provided in the form of particles or powder that cover(s) a surface of the support. The photocatalyst provided in such a form may be fixed to the surface of the support by sintering.

Specifically, a slurry containing particles of the photocatalyst dispersed therein is applied to the support, and the support is then sintered, whereby the catalyst body 31 including support and the photocatalyst fixed to the surface of the support can be produced.

The frame 32 can be made of, for example, a resin molding. The frame 32 can be formed into a shape that holds, between its portions, the catalyst body 31. The frame 32 can have a portion for retaining an outer peripheral portion of the catalyst body 31 and a portion extending across the catalyst body 31.

A lower limit of the distance between the catalyst member 30 and the first inner wall surface 21 is preferably 1 mm, and more preferably 2 mm, in order to cause air to flow smoothly. On the other hand, an upper limit of the distance between the catalyst member 30 and the first inner wall surface 21 is preferably 8 mm, and more preferably 5 mm, in order to efficiently bring air into contact with the photocatalyst.

A lower limit of the distance between the catalyst member 30 and the second inner wall surface 41 is preferably 4 mm, and more preferably 6 mm, in order to uniformly irradiate the catalyst member 30 with light. On the other hand, an upper limit of the distance between the catalyst member 30 and the second inner wall surface 41 is preferably 12 mm, and more preferably 10 mm, in order to efficiently bring air into contact with the photocatalyst. Further, it is preferable that the distance between the catalyst member 30 and the second inner wall surface 41 is greater than the distance between the catalyst member 30 and the first inner wall surface 21.

The intermediate base 40 has a top plate 42 that provides the second inner wall surface 41 of the air passage 4, a fan housing part 43 in which the exhaust fan 60 is housed, and a second current plate 44 that is provided in the inlet portion of the air passage 4, extends from above (from a side adjacent to the second inner wall surface 41), and stretches over the entire width of the air passage 4. The intermediate base 40 further has a pressing structure, such as a projection or a stepped portion, that presses the catalyst member 30 onto the holding structure of the lower casing 10. The intermediate base 40, which has the complex shape as described above, can be made of a resin molding.

The circuit board 50 and the exhaust fan 60 are fastened to the intermediate base 40. Further, electric elements, such as a power supply 45 for supplying power to the circuit board 50 and the exhaust fan 60, are all disposed on the intermediate base 40. This configuration eliminates the need to provide a connector for electric connection, between the upper half and the lower half.

The top plate 42 has a plurality of light-projecting apertures 46 dispersed in a region of the top plate 42 facing the catalyst body 31. The light-projecting apertures 46 are provided for irradiation of light that activates the catalyst member 30, the light being emitted from the circuit board 50 to be described later. Each light-projecting aperture 46 preferably increases in size toward the air passage 4 such that a large area can be irradiated with the light.

The fan housing part 43 has, in its portion adjacent to the top plate 42, a communication opening 47 (see FIG. 2) that allows a space outside (space above) the circuit board 50 that is layered on the top plate 42 to communicate with a passage adjacent to a suction side of the exhaust fan 60. The communication opening 47 has a cross-sectional area that is sufficiently smaller than the cross-sectional area of the air passage 4. The exhaust fan 60 suctions a small amount of air from the space above the circuit board 50. A flow of air suctioned through the communication opening 47 exerts an effect of cooling the circuit board 50. The communication opening 47 of the present embodiment is formed as a slit. However, the communication opening 47 may have any shape.

The second current plate 44 and the first current plate 11 form, in the inlet portion of the air passage 4, a labyrinth structure that makes it impossible to directly see a downstream portion of the air passage 4 from an upstream portion. The first current plate 11 and the second current plate 44 reduce the height of the passage, thereby making the local passage cross-sectional area smaller than the passage cross-sectional area between the first inner wall surface 21 and the second inner wall surface 41. This configuration can prevent air from flowing through, so that air can be supplied to the entire air passage 4 and contact of air with the catalyst member 30 can be facilitated.

The circuit board 50 is disposed in full contact with the upper surface of the top plate 42 and closes the plurality of light-projecting apertures 46 from above, thereby defining a plurality of recesses in the second inner wall surface 41. In other words, The circuit board 50 forms end walls of the plurality of recesses of the second inner wall surface 41. The circuit board 50 has a plurality of light sources 51 that are mounted to be received in the light-projecting apertures 46 on a one-to-one basis, and that emit light for activating the catalyst member 30. Each light source 51 is received in an associated one of the light-projecting apertures 46, i.e., an associated one of the recesses in the second inner wall surface 41 such that the light source 51 does not protrude from the second inner wall surface 41 toward the air passage 4. Examples of the light sources 51 include a UV light-emitting diode.

Thus, this configuration, in which the plurality of small light sources 51 are dispersed to be received in the recesses in the second inner wall surface 41 on a one-to-one basis, makes it possible to activate the entire catalyst member 30 even though the catalyst member 30 having a relatively large area is disposed in the air passage 4 that is flat and has a relatively small volumetric capacity. This feature makes it possible to purify air by degrading organic matter and the like contained in air, while inhibiting the air purifier 1 from increasing in size. Further, the configuration, in which the light sources 51 are received in the recesses without protruding from the second inner wall surface 41, does not impede the air flow in the air passage 4, thereby making it possible to facilitate efficient contact of air with the catalyst member 30.

The exhaust fan 60 is housed in the fan housing part 43 of the intermediate base 40, while a space is left adjacent to the top plate 42, the space functioning as a suction passage. As the exhaust fan 60, a centrifugal fan is suitably used which has a relatively high static pressure.

The upper casing 70 is detachably combined with the lower casing 10, and forms, together with the lower casing 10, a casing that houses functional elements of the air purifier 1. The upper casing 70 is connected to the intermediate base 40 and covers the electric elements including the circuit board 50. This configuration, in which the electric elements are housed in the upper half, makes it possible to prevent a user from receiving an electric shock. The upper casing 70 has an exhaust passage-forming part 71 that guides air sent from the exhaust fan 60 to the air outlet 3. The upper casing 70 having the above-described configuration can be made of a resin molding.

The cover 80 that covers the upper casing 70 is provided for improvement of design of the air purifier 1. From the viewpoint of function, the cover 80 may be omitted. Since the cover 80 has a simple structure, it may be made of, for example, a metal pressing, whereby texture of the air purifier 1 can be improved.

The decorative central member 90 is attached to close the central opening of the air purifier 1 in order to further improve the design. Especially, the decorative central member 90 may be omitted, or may be replaced with a member that imparts a different design and an additional function, such as a member having hands of a clock or a lighting device.

The air purifier 1 with the above-described configuration defines, between the first inner wall surface 21 and the second inner wall surface 41, the air passage 4 having a flat passage cross section and meandering in a plane perpendicular to a thickness direction. The catalyst member 30 having a flat mesh shape is disposed in the air passage 4, and is activated by light emitted from the plurality of light sources 51 dispersed on the second inner wall surface 41. This feature allows the catalyst member 30 to have a large area relative to the volumetric capacity of the air passage 4. As a result, the air purifier 1 is small and capable of degrading organic matter highly efficiently.

Since the air purifier 1 is small and has an excellent design, it can be used in various ways. For example, the air purifier 1 can be attached to the top of a pole member, such as a clothes tree, can be hung from a ceiling while being oriented upside down, or can be attached to a wall while having its center axis extending horizontally. In these cases, the decorative central member 90 can be replaced with an appropriate member as described above, thereby providing an advantage that the air purifier 1 can have a further improved design and an additional function.

In the foregoing, the air purifier according to an embodiment of the present disclosure has been described. However, the above-described configuration and effects of the air purifier are not intended to limit the present disclosure. For example, the shape of the air purifier of the present disclosure is not limited to the doughnut shape, but may be any shape, such as a rectangular shape or a triangular shape.

EXPLANATION OF REFERENCE NUMERALS

1: Air Purifier
2: Air Inlet
3: Air Outlet
4: Air Passage
10: Lower Casing
11: First Current Plate
12: Filter Member
20: Guide Plate
21: First Inner Wall Surface
30: Catalyst Member
31: Catalyst Body
32: Frame
40: Intermediate Base
41: Second Inner Wall Surface
42: Top Plate
43: Fan Housing Part
44: Second Current Plate
45: Power Supply
46: Light-Projecting Aperture
47: Communication Opening
50: Circuit Board
51: Light Source
60: Exhaust Fan
70: Upper Casing
71: Exhaust Passage-Forming Part
80: Cover
90: Decorative Central Member

What is claimed is:

1. An air purifier comprising:
    an air passage defined between a first inner wall surface and a second inner wall surface that are planar and face each other, having a flat passage cross section in which the first inner wall surface and the second inner wall surface are separated from one another in a thickness direction, and meandering in a plane parallel to the first inner wall surface and the second inner wall surface, the meandering comprising a portion of the air passage curving about an axis extending in the thickness direction;
    a catalyst member including a support having a flat mesh shape, and a photocatalyst supported on the support, the catalyst member being disposed parallel to the first inner wall surface and the second inner wall surface in the air passage; and
    a plurality of light sources dispersed on the second inner wall surface, and configured to irradiate the catalyst member with light that activates the photocatalyst.

2. The air purifier according to claim 1, further comprising:
    a first current plate extending from a side adjacent to the first inner wall surface and a second current plate extending from a side adjacent to the second inner wall surface, the first and second current plates forming a labyrinth structure in an inlet portion of the air passage.

3. The air purifier according to claim 1,
    wherein the plurality of light sources are received in recesses formed in the second inner wall surface, on a one-to-one basis.

4. The air purifier according to claim 3, further comprising:
    an exhaust fan configured to suction air out of the air passage, and
    a circuit board having the plurality of light sources mounted thereto, and forming end walls of the recesses,
    wherein a space outside the circuit board communicates with a passage adjacent to a suction side of the exhaust fan through an opening having a smaller cross-sectional area than the air passage.

5. The air purifier according to claim 1, further comprising:
    a casing having a holding structure that holds the catalyst member; and
    a smooth guide plate disposed in the casing and forming the first inner wall surface.

6. The air purifier according to claim 5, further comprising:
    an intermediate base forming the second inner wall surface and having an electric element disposed thereon,
    wherein the casing has a lower casing that has the guide plate fastened thereto, and an upper casing that is detachably combined with the lower casing, has the intermediate base fastened thereto, and covers the electric element.

7. The air purifier according to claim 1,
    wherein a distance between the catalyst member and the first inner wall surface is 1 mm or more and 8 mm or less, and
    wherein a distance between the catalyst member and the second inner wall surface is 4 mm or more and 12 mm or less, and is greater than the distance between the catalyst member and the first inner wall surface.

\* \* \* \* \*